US008997753B2

(12) United States Patent
Li et al.

(10) Patent No.: US 8,997,753 B2
(45) Date of Patent: Apr. 7, 2015

(54) ELECTRONIC SMOKING ARTICLE

(71) Applicant: Altria Client Services Inc., Richmond, VA (US)

(72) Inventors: San Li, Midlothian, VA (US); George Karles, Richmond, VA (US); Munmaya K. Mishra, Manakin Sabot, VA (US); Weiling Li, Moseley, VA (US); Barry S. Smith, Hopewell, VA (US); Ali A. Rostami, Glen Allen, VA (US); Christopher S. Tucker, Midlothian, VA (US); Geoffrey Brandon Jordan, Midlothian, VA (US)

(73) Assignee: Altria Client Services Inc., Richmond, VA (US)

( * ) Notice: Subject to any disclaimer, the term of this patent is extended or adjusted under 35 U.S.C. 154(b) by 0 days.

(21) Appl. No.: 13/756,067

(22) Filed: Jan. 31, 2013

(65) Prior Publication Data

US 2013/0192621 A1 Aug. 1, 2013

Related U.S. Application Data

(60) Provisional application No. 61/593,004, filed on Jan. 31, 2012.

(51) Int. Cl.

| | |
|---|---|
| ***A24F 47/00*** | (2006.01) |
| ***H01C 17/00*** | (2006.01) |

(52) U.S. Cl.

CPC ............. *A24F 47/008* (2013.01); *A24F 47/004* (2013.01); *H01C 17/00* (2013.01)

(58) Field of Classification Search

USPC ......................... 131/194, 270, 273, 328–330; 128/202.21

See application file for complete search history.

(56) References Cited

U.S. PATENT DOCUMENTS

| | | | |
|---|---|---|---|
| 393,869 | A | 12/1888 | Warren |
| 539,839 | A | 5/1895 | Voron |
| 567,558 | A | 9/1896 | Wiseman |
| 652,987 | A | 7/1900 | Watson |
| 962,617 | A | 6/1910 | Bucceri |
| 1,013,157 | A | 1/1912 | Hadaway, Jr. |
| 1,514,682 | A | 11/1924 | Wilson |
| 1,771,366 | A | 7/1930 | Wyss et al. |
| 1,775,947 | A | 9/1930 | Robinson |
| 1,968,509 | A | 7/1934 | Tiffany |
| 2,051,030 | A | 8/1936 | Dalinda |

(Continued)

FOREIGN PATENT DOCUMENTS

| | | |
|---|---|---|
| BE | 421623 | 6/1937 |
| CA | 1202378 | 3/1986 |

(Continued)

OTHER PUBLICATIONS

International Search Report and Written Opinion for PCT/US13/24228 dated Apr. 9, 2013.

(Continued)

*Primary Examiner* — Richard Crispino
*Assistant Examiner* — Eric Yaary
(74) *Attorney, Agent, or Firm* — Harness, Dickey & Pierce, P.L.C.

(57) ABSTRACT

An electronic smoking article comprising an aerosol generator and a mechanical aerosol converter insert having the capacity to improve characteristics of aerosol produced by the aerosol generator, including sensory attributes.

19 Claims, 6 Drawing Sheets

(56) References Cited

U.S. PATENT DOCUMENTS 2,057,353 A 10/1936 Whittemore, Jr.
2,104,266 A 1/1938 McCormick
2,247,869 A 7/1940 Beers
2,342,853 A 2/1944 Furstenberg
2,406,275 A 8/1946 Wejnarth
2,425,624 A 8/1947 Lardinois
2,442,004 A 5/1948 Hayward-Butt
2,445,476 A 7/1948 Folkman
2,479,002 A 8/1949 Ceperly
2,558,127 A 6/1951 Downs
2,631,219 A 3/1953 Suchy
2,701,836 A 2/1955 Pavenick
2,702,033 A 2/1955 Pardeman
2,721,551 A 10/1955 Lobl
2,746,890 A 5/1956 Legler
2,815,028 A 12/1957 Bernhard
2,830,597 A 4/1958 Kummli
2,836,183 A 5/1958 Fay et al.
2,860,638 A 11/1958 Bartolomeo
2,907,686 A 10/1959 Siegel
2,971,039 A 2/1961 Western
2,972,557 A 2/1961 Toulmin, Jr.
2,974,669 A 3/1961 Ellis
3,062,218 A 11/1962 Temkovits
3,150,668 A 9/1964 Lassiter et al.
3,200,819 A 8/1965 Gilbert
3,234,357 A 2/1966 Seuthe
3,255,760 A 6/1966 Selker
3,258,015 A 6/1966 Ellis et al.
3,280,819 A 10/1966 Weeks
3,320,953 A 5/1967 Rindner
3,324,861 A 6/1967 Gaisman
3,347,231 A 12/1967 Ellis et al.
3,356,094 A 12/1967 Ellis et al.
3,363,633 A 1/1968 Weber
3,402,723 A 9/1968 Hu
3,404,692 A 10/1968 Lampert
3,410,273 A 11/1968 Bolles
3,425,414 A 2/1969 Roche
3,482,580 A 12/1969 Hollabaugh
3,516,417 A 6/1970 Moses
3,521,643 A 7/1970 Toth
3,559,300 A 2/1971 Fox
3,587,573 A 6/1971 Flack
3,608,560 A 9/1971 Briskin et al.
3,631,856 A 1/1972 Taylor
3,648,929 A 3/1972 Corbaz
3,681,018 A 8/1972 Knauff
3,683,936 A 8/1972 O'Neil, Jr.
3,721,240 A 3/1973 Tamburri
3,738,374 A 6/1973 Bennett
3,744,496 A 7/1973 McCarty et al.
D229,725 S 12/1973 Berger
D229,788 S 1/1974 Berger
D229,789 S 1/1974 Berger
D229,790 S 1/1974 Berger
3,789,840 A 2/1974 Rosenblatt
3,804,100 A 4/1974 Fariello
3,875,476 A 4/1975 Crandall et al.
3,878,041 A 4/1975 Leitnaker et al.
3,886,954 A 6/1975 Hannema et al.
3,889,690 A 6/1975 Guarnieri
3,895,219 A 7/1975 Richerson et al.
3,943,941 A 3/1976 Boyd et al.
D240,541 S 7/1976 Rupert
4,016,061 A 4/1977 Wasa et al.
4,068,672 A 1/1978 Guerra
4,077,784 A 3/1978 Vayrynen
4,083,372 A 4/1978 Boden
4,098,725 A 7/1978 Yamamoto et al.
4,110,260 A 8/1978 Yamamoto et al.
4,131,119 A 12/1978 Blasutti
4,141,369 A 2/1979 Burruss
4,149,548 A 4/1979 Bradshaw
4,164,230 A 8/1979 Pearlman
4,171,000 A 10/1979 Uhle
4,184,496 A 1/1980 Adair
4,193,411 A 3/1980 Faris et al.
4,209,026 A 6/1980 Dock
4,215,708 A 8/1980 Bron
4,219,032 A 8/1980 Tabatznik et al.
4,246,913 A 1/1981 Ogden et al.
4,256,945 A 3/1981 Carter et al.
4,259,970 A 4/1981 Green, Jr.
4,267,976 A 5/1981 Chatwin
4,275,747 A 6/1981 Miller
4,284,089 A 8/1981 Ray
4,303,083 A 12/1981 Burruss, Jr.
4,319,587 A 3/1982 Moser
4,319,591 A 3/1982 Keith et al.
4,327,186 A 4/1982 Murata et al.
4,331,166 A 5/1982 Hale
4,340,072 A 7/1982 Bolt et al.
4,393,884 A 7/1983 Jacobs
D270,097 S 8/1983 Minkevitch
4,407,971 A 10/1983 Komatsu et al.
4,413,641 A * 11/1983 Dwyer et al. ................ 131/361
4,416,840 A 11/1983 Lee et al.
4,418,354 A 11/1983 Perduijn
4,419,302 A 12/1983 Nishino et al.
4,429,703 A 2/1984 Haber
4,431,903 A 2/1984 Riccio
4,436,100 A 3/1984 Green, Jr.
4,449,039 A 5/1984 Fukazawa et al.
4,457,319 A 7/1984 Lamb et al.
4,463,247 A 7/1984 Lawrence et al.
4,475,029 A 10/1984 Yoshida et al.
4,493,331 A 1/1985 Porenski, Jr.
4,503,319 A 3/1985 Moritoki et al.
4,505,282 A 3/1985 Cogbill et al.
4,515,763 A 5/1985 Boudart et al.
4,517,996 A 5/1985 Vester
4,528,121 A 7/1985 Matsushita et al.
4,549,905 A 10/1985 Yamaguchi et al.
4,555,358 A 11/1985 Matsushita et al.
4,562,337 A 12/1985 Lawrence
4,570,646 A 2/1986 Herron
4,580,583 A 4/1986 Green, Jr.
4,621,649 A 11/1986 Osterrath
4,623,401 A 11/1986 Derbyshire et al.
4,624,828 A 11/1986 Alexander
4,634,837 A 1/1987 Ito et al.
4,637,407 A 1/1987 Bonanno et al.
4,649,944 A 3/1987 Houck, Jr. et al.
4,659,912 A 4/1987 Derbyshire
4,676,237 A 6/1987 Wood et al.
4,687,008 A 8/1987 Houck, Jr. et al.
4,708,151 A 11/1987 Shelar
4,714,082 A 12/1987 Banerjee et al.
4,735,217 A 4/1988 Gerth et al.
4,765,347 A 8/1988 Sensabaugh et al.
4,771,796 A 9/1988 Myer
4,776,353 A 10/1988 Lilja et al.
4,780,299 A 10/1988 Kumagai et al.
4,784,978 A 11/1988 Ogasawara et al.
4,793,365 A 12/1988 Sensabaugh, Jr. et al.
4,799,979 A 1/1989 Baldi
4,800,183 A 1/1989 Quinby
4,800,903 A 1/1989 Ray et al.
4,804,002 A 2/1989 Herron
4,837,421 A 6/1989 Luthy
4,846,199 A 7/1989 Rose
4,848,376 A 7/1989 Lilja et al.
4,851,206 A 7/1989 Boudart et al.
4,874,924 A 10/1989 Yamamoto et al.
4,877,989 A 10/1989 Drews et al.
4,922,901 A 5/1990 Brooks et al.
4,941,486 A 7/1990 Dube et al.
4,945,929 A * 8/1990 Egilmex ....................... 131/273
4,945,931 A 8/1990 Gori
4,947,874 A 8/1990 Brooks et al.
4,947,875 A 8/1990 Brooks
4,953,572 A * 9/1990 Rose et al. .................... 131/270
4,966,171 A 10/1990 Serrano et al.

(56) References Cited

U.S. PATENT DOCUMENTS

| | | | |
|---|---|---|---|
| 4,981,522 A | 1/1991 | Nichols et al. | |
| 4,991,606 A | 2/1991 | Serrano et al. | |
| 4,993,436 A | 2/1991 | Bloom, Jr. | |
| 5,016,656 A | 5/1991 | McMurtrie | |
| 5,038,458 A | 8/1991 | Wagoner et al. | |
| 5,040,552 A | 8/1991 | Schleich et al. | |
| 5,042,470 A | 8/1991 | Kanesaka | |
| 5,042,510 A | 8/1991 | Curtiss et al. | |
| 5,045,237 A | 9/1991 | Washburn | |
| 5,060,671 A | 10/1991 | Counts et al. | |
| 5,076,296 A | 12/1991 | Nystrom et al. | |
| 5,085,804 A | 2/1992 | Washburn | |
| 5,093,894 A | 3/1992 | Deevi et al. | |
| 5,095,921 A | 3/1992 | Losee et al. | |
| 5,116,298 A | 5/1992 | Bondanelli et al. | |
| 5,137,578 A | 8/1992 | Chan | |
| 5,139,594 A | 8/1992 | Rabin | |
| 5,144,962 A | 9/1992 | Counts et al. | |
| 5,144,964 A | 9/1992 | Demain | |
| 5,157,242 A | 10/1992 | Hetherington et al. | |
| 5,159,940 A | 11/1992 | Hayward et al. | |
| 5,179,966 A | 1/1993 | Losee et al. | |
| 5,188,130 A | 2/1993 | Hajaligol et al. | |
| 5,224,498 A | 7/1993 | Deevi et al. | |
| 5,228,460 A | 7/1993 | Sprinkel et al. | |
| 5,235,157 A | 8/1993 | Blackburn | |
| 5,249,586 A | 10/1993 | Morgan et al. | |
| 5,269,327 A | 12/1993 | Counts et al. | |
| 5,274,214 A | 12/1993 | Blackburn | |
| 5,285,050 A | 2/1994 | Blackburn | |
| 5,304,125 A * | 4/1994 | Leith | 604/57 |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen | |
| 5,388,594 A | 2/1995 | Counts et al. | |
| 5,396,911 A | 3/1995 | Casey, III et al. | |
| 5,408,574 A | 4/1995 | Deevi et al. | |
| 5,479,948 A | 1/1996 | Counts et al. | |
| 5,497,791 A | 3/1996 | Bowen et al. | |
| 5,498,855 A | 3/1996 | Deevi et al. | |
| 5,499,636 A | 3/1996 | Baggett, Jr. et al. | |
| 5,505,214 A | 4/1996 | Collins et al. | |
| 5,514,630 A | 5/1996 | Willkens et al. | |
| 5,530,225 A | 6/1996 | Hajaligol | |
| 5,591,368 A | 1/1997 | Fleischhauer et al. | |
| 5,592,955 A | 1/1997 | Keritsis | |
| 5,595,706 A | 1/1997 | Sikka et al. | |
| 5,611,360 A | 3/1997 | Tang | |
| 5,613,504 A | 3/1997 | Collins et al. | |
| 5,613,505 A | 3/1997 | Campbell et al. | |
| 5,665,262 A | 9/1997 | Hajaligol et al. | |
| 5,666,976 A | 9/1997 | Adams et al. | |
| 5,666,977 A | 9/1997 | Higgins et al. | |
| 5,666,978 A | 9/1997 | Counts et al. | |
| 5,692,525 A | 12/1997 | Counts et al. | |
| 5,708,258 A | 1/1998 | Counts et al. | |
| 5,724,997 A | 3/1998 | Smith et al. | |
| 5,726,421 A | 3/1998 | Fleischhauer et al. | |
| 5,730,158 A | 3/1998 | Collins et al. | |
| 5,738,087 A * | 4/1998 | King | 128/200.23 |
| 5,743,251 A | 4/1998 | Howell et al. | |
| 5,750,964 A | 5/1998 | Counts et al. | |
| 5,758,637 A | 6/1998 | Ivri et al. | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,909,845 A | 6/1999 | Greatbatch et al. | |
| 5,915,387 A | 6/1999 | Baggett, Jr. et al. | |
| 5,934,289 A | 8/1999 | Watkins et al. | |
| 5,935,975 A | 8/1999 | Rose et al. | |
| 5,954,979 A | 9/1999 | Counts et al. | |
| 5,962,526 A | 10/1999 | Yu et al. | |
| 5,988,176 A | 11/1999 | Baggett, Jr. et al. | |
| 6,026,820 A | 2/2000 | Baggett, Jr. et al. | |
| 6,040,560 A | 3/2000 | Fleischhauer et al. | |
| 6,053,176 A | 4/2000 | Adams et al. | |
| 6,085,740 A | 7/2000 | Ivri et al. | |
| 6,116,247 A | 9/2000 | Banyasz et al. | |
| 6,125,866 A | 10/2000 | Nichols et al. | |
| 6,155,268 A | 12/2000 | Takeuchi | |
| 6,156,796 A | 12/2000 | Sano et al. | |
| 6,196,218 B1 | 3/2001 | Voges | |
| 6,214,133 B1 | 4/2001 | Deevi et al. | |
| 6,223,745 B1 * | 5/2001 | Hammarlund et al. | 128/200.18 |
| 6,234,167 B1 | 5/2001 | Cox et al. | |
| 6,280,682 B1 | 8/2001 | Sikka et al. | |
| D453,854 S | 2/2002 | Verhoeven-Koster et al. | |
| 6,357,671 B1 | 3/2002 | Cewers | |
| 6,418,938 B1 | 7/2002 | Fleischhauer et al. | |
| 6,425,964 B1 | 7/2002 | Deevi et al. | |
| 6,427,682 B1 | 8/2002 | Klimowicz et al. | |
| 6,443,146 B1 | 9/2002 | Voges | |
| 6,446,426 B1 | 9/2002 | Sweeney et al. | |
| 6,491,233 B2 | 12/2002 | Nichols | |
| 6,501,052 B2 | 12/2002 | Cox et al. | |
| 6,506,338 B1 | 1/2003 | Gedevanishvili et al. | |
| 6,509,553 B2 | 1/2003 | Golan et al. | |
| 6,532,965 B1 | 3/2003 | Abhulimen et al. | |
| 6,557,552 B1 | 5/2003 | Cox et al. | |
| 6,568,390 B2 | 5/2003 | Nichols et al. | |
| 6,598,607 B2 | 7/2003 | Adiga et al. | |
| D478,983 S | 8/2003 | Whitehall et al. | |
| 6,607,576 B1 | 8/2003 | Sikka et al. | |
| 6,640,050 B2 | 10/2003 | Nichols et al. | |
| 6,681,998 B2 | 1/2004 | Sharpe et al. | |
| 6,682,716 B2 | 1/2004 | Hodges et al. | |
| 6,688,313 B2 | 2/2004 | Wrenn et al. | |
| 6,701,921 B2 | 3/2004 | Sprinkel, Jr. et al. | |
| 6,701,922 B2 | 3/2004 | Hindle et al. | |
| 6,715,487 B2 | 4/2004 | Nichols et al. | |
| 6,766,220 B2 | 7/2004 | McRae et al. | |
| 6,772,756 B2 | 8/2004 | Shayan | |
| 6,799,572 B2 | 10/2004 | Nichols et al. | |
| 6,803,545 B2 | 10/2004 | Blake et al. | |
| 6,803,550 B2 | 10/2004 | Sharpe et al. | |
| 6,804,458 B2 | 10/2004 | Sherwood et al. | |
| 6,806,682 B2 | 10/2004 | Hsiao | |
| 6,810,883 B2 | 11/2004 | Felter et al. | |
| 6,854,470 B1 | 2/2005 | Pu | |
| 6,883,516 B2 | 4/2005 | Hindle et al. | |
| D512,777 S | 12/2005 | Beisner et al. | |
| 7,077,130 B2 | 7/2006 | Nichols et al. | |
| 7,117,867 B2 | 10/2006 | Cox et al. | |
| 7,131,599 B2 | 11/2006 | Katase | |
| 7,167,641 B2 | 1/2007 | Tam et al. | |
| 7,167,776 B2 | 1/2007 | Maharajh et al. | |
| 7,173,222 B2 | 2/2007 | Cox et al. | |
| 7,293,565 B2 | 11/2007 | Griffin et al. | |
| 7,381,277 B2 | 6/2008 | Gonterman et al. | |
| 7,400,940 B2 | 7/2008 | McRae et al. | |
| 7,404,405 B1 | 7/2008 | Mehio | |
| 7,405,555 B2 | 7/2008 | Rao et al. | |
| 7,458,374 B2 | 12/2008 | Hale et al. | |
| D590,988 S | 4/2009 | Hon | |
| D590,989 S | 4/2009 | Hon | |
| D590,990 S | 4/2009 | Hon | |
| D590,991 S | 4/2009 | Hon | |
| 7,527,059 B2 | 5/2009 | Iannuzzi | |
| 7,614,402 B2 | 11/2009 | Gomes | |
| D613,902 S | 4/2010 | Kaljura | |
| D613,903 S | 4/2010 | Wu et al. | |
| D613,904 S | 4/2010 | Wu et al. | |
| D614,346 S | 4/2010 | Lik | |
| 7,726,320 B2 | 6/2010 | Robinson et al. | |
| 7,789,089 B2 | 9/2010 | Dube et al. | |
| 7,810,505 B2 | 10/2010 | Yang | |
| 7,810,508 B2 | 10/2010 | Wyss-Peters et al. | |
| 7,832,397 B2 | 11/2010 | Lipowicz | |
| 7,832,410 B2 | 11/2010 | Hon | |
| 7,845,359 B2 | 12/2010 | Montaser | |
| 7,878,962 B2 | 2/2011 | Karles et al. | |

(56) References Cited

U.S. PATENT DOCUMENTS

| | | | |
|---|---|---|---|
| 7,906,936 | B2 | 3/2011 | Azancot |
| 7,913,688 | B2 | 3/2011 | Cross et al. |
| 7,920,777 | B2 | 4/2011 | Rabin et al. |
| 7,938,124 | B2 | 5/2011 | Izumiya et al. |
| 7,952,322 | B2 | 5/2011 | Partovi et al. |
| D644,375 | S | 8/2011 | Zhou |
| 7,997,280 | B2 | 8/2011 | Rosenthal |
| D646,431 | S | 10/2011 | Awty et al. |
| 8,052,127 | B2 | 11/2011 | Nichols et al. |
| D651,338 | S | 12/2011 | Awty et al. |
| 8,079,371 | B2 | 12/2011 | Robinson et al. |
| D652,987 | S | 1/2012 | Kaljura |
| D653,390 | S | 1/2012 | Kaljura |
| D653,802 | S | 2/2012 | Kaljura |
| D655,036 | S | 2/2012 | Zhou |
| 8,113,215 | B2 | 2/2012 | Rasouli et al. |
| 8,118,161 | B2 | 2/2012 | Guerrera et al. |
| D656,094 | S | 3/2012 | Wu |
| 8,127,772 | B2 | 3/2012 | Montaser |
| 8,156,944 | B2 | 4/2012 | Han |
| 8,157,918 | B2 | 4/2012 | Becker et al. |
| 8,205,622 | B2 | 6/2012 | Pan |
| 8,251,055 | B2 | 8/2012 | Srinivasan |
| 8,258,192 | B2 | 9/2012 | Wu et al. |
| D671,677 | S | 11/2012 | Wu |
| D671,678 | S | 11/2012 | Wu |
| 8,314,591 | B2 | 11/2012 | Terry et al. |
| D677,000 | S | 2/2013 | Liu |
| D677,001 | S | 2/2013 | Liu |
| 8,365,742 | B2 | 2/2013 | Han |
| 8,371,310 | B2 | 2/2013 | Brenneise |
| 8,375,957 | B2 | 2/2013 | Hon |
| 8,393,331 | B2 | 3/2013 | Hon et al. |
| D681,268 | S | 4/2013 | Wu |
| D681,269 | S | 4/2013 | Wu |
| D683,898 | S | 6/2013 | Liu |
| D683,899 | S | 6/2013 | Liu |
| D684,311 | S | 6/2013 | Liu |
| 8,459,270 | B2 | 6/2013 | Coven et al. |
| D688,418 | S | 8/2013 | Liu |
| 8,499,766 | B1 | 8/2013 | Newton |
| 8,511,318 | B2 | 8/2013 | Hon et al. |
| D690,461 | S | 9/2013 | Chen |
| 8,528,569 | B1 | 9/2013 | Newton |
| D691,765 | S | 10/2013 | Tucker et al. |
| D691,766 | S | 10/2013 | Tucker et al. |
| 8,550,068 | B2 | 10/2013 | Terry et al. |
| 8,550,069 | B2 | 10/2013 | Alelov |
| 8,558,147 | B2 | 10/2013 | Greim et al. |
| 8,578,942 | B2 | 11/2013 | Schennum |
| D695,449 | S | 12/2013 | Tucker et al. |
| 8,662,479 | B2 | 3/2014 | Nichols et al. |
| 8,689,804 | B2 | 4/2014 | Fernando et al. |
| 8,689,805 | B2 | 4/2014 | Hon et al. |
| 8,794,231 | B2 | 8/2014 | Thorens et al. |
| 2003/0205228 | A1 | 11/2003 | Nichols et al. |
| 2004/0020500 | A1 | 2/2004 | Wrenn et al. |
| 2004/0035409 | A1 | 2/2004 | Harwig et al. |
| 2004/0050396 | A1 | 3/2004 | Squeo |
| 2004/0079368 | A1 | 4/2004 | Gupta et al. |
| 2004/0081624 | A1 | 4/2004 | Nguyen et al. |
| 2004/0099266 | A1 | 5/2004 | Cross et al. |
| 2004/0105818 | A1 | 6/2004 | Every et al. |
| 2004/0129793 | A1 | 7/2004 | Nguyen et al. |
| 2004/0170405 | A1 | 9/2004 | Sherwood et al. |
| 2004/0200493 | A1 | 10/2004 | Matsufuji et al. |
| 2004/0223917 | A1 | 11/2004 | Hindle et al. |
| 2004/0223918 | A1 | 11/2004 | Pham et al. |
| 2004/0255941 | A1 | 12/2004 | Nichols et al. |
| 2005/0016550 | A1 | 1/2005 | Katase |
| 2005/0016553 | A1 | 1/2005 | Iannuzzi |
| 2005/0045179 | A1 | 3/2005 | Faison et al. |
| 2005/0079137 | A1 | 4/2005 | Blondino et al. |
| 2005/0081639 | A1 | 4/2005 | Gourlay |
| 2005/0126624 | A1 | 6/2005 | Pellizzari |
| 2005/0132879 | A1 | 6/2005 | Grollimund et al. |
| 2005/0133029 | A1 | 6/2005 | Nichols et al. |
| 2005/0143866 | A1 | 6/2005 | McRae et al. |
| 2005/0175331 | A1 | 8/2005 | Tam et al. |
| 2005/0205084 | A1 | 9/2005 | Gupta et al. |
| 2005/0268911 | A1 | 12/2005 | Cross et al. |
| 2005/0279371 | A1 | 12/2005 | Billard et al. |
| 2006/0016453 | A1 | 1/2006 | Kim |
| 2006/0047368 | A1 | 3/2006 | Maharajh et al. |
| 2006/0191546 | A1 | 8/2006 | Tokano et al. |
| 2006/0196518 | A1 | 9/2006 | Hon |
| 2006/0254604 | A1 | 11/2006 | Martinez Fernandez |
| 2007/0074734 | A1 | 4/2007 | Braunshteyn et al. |
| 2007/0095357 | A1 | 5/2007 | Besso et al. |
| 2007/0102013 | A1 | 5/2007 | Adams et al. |
| 2007/0175476 | A1* | 8/2007 | Lipowicz ................. 128/205.29 |
| 2007/0267031 | A1* | 11/2007 | Hon .............................. 131/273 |
| 2007/0267032 | A1 | 11/2007 | Shan |
| 2007/0279002 | A1 | 12/2007 | Partovi |
| 2008/0047571 | A1* | 2/2008 | Braunshteyn et al. ........ 131/202 |
| 2008/0092912 | A1 | 4/2008 | Robinson et al. |
| 2008/0110458 | A1 | 5/2008 | Srinivasan et al. |
| 2008/0230052 | A1 | 9/2008 | Montaser |
| 2008/0276947 | A1 | 11/2008 | Martzel |
| 2009/0007925 | A1 | 1/2009 | Rasouli et al. |
| 2009/0044816 | A1 | 2/2009 | Rasouli et al. |
| 2009/0056729 | A1 | 3/2009 | Zawadzki et al. |
| 2009/0084391 | A1 | 4/2009 | Krupp |
| 2009/0095311 | A1 | 4/2009 | Han |
| 2009/0107503 | A1* | 4/2009 | Baran ....................... 128/204.25 |
| 2009/0126745 | A1 | 5/2009 | Hon |
| 2009/0133704 | A1 | 5/2009 | Strickland et al. |
| 2009/0151717 | A1 | 6/2009 | Bowen et al. |
| 2009/0162294 | A1 | 6/2009 | Werner |
| 2009/0188490 | A1 | 7/2009 | Han |
| 2009/0230117 | A1 | 9/2009 | Fernando et al. |
| 2009/0272379 | A1 | 11/2009 | Thorens et al. |
| 2009/0283103 | A1 | 11/2009 | Nielsen et al. |
| 2009/0301502 | A1 | 12/2009 | Mehio |
| 2009/0320863 | A1 | 12/2009 | Fernando et al. |
| 2010/0031967 | A1 | 2/2010 | Inagaki |
| 2010/0031968 | A1 | 2/2010 | Sheikh et al. |
| 2010/0083959 | A1 | 4/2010 | Siller |
| 2010/0126505 | A1 | 5/2010 | Rinker |
| 2010/0163063 | A1 | 7/2010 | Fernando et al. |
| 2010/0200008 | A1 | 8/2010 | Taieb |
| 2010/0206317 | A1 | 8/2010 | Albino et al. |
| 2010/0242975 | A1 | 9/2010 | Hearn |
| 2010/0242976 | A1 | 9/2010 | Katayama et al. |
| 2010/0307518 | A1 | 12/2010 | Wang |
| 2011/0005535 | A1 | 1/2011 | Xiu |
| 2011/0011396 | A1 | 1/2011 | Fang |
| 2011/0036346 | A1 | 2/2011 | Cohen et al. |
| 2011/0036363 | A1 | 2/2011 | Urtsev et al. |
| 2011/0088707 | A1 | 4/2011 | Hajaligol |
| 2011/0094523 | A1* | 4/2011 | Thorens et al. ............... 131/194 |
| 2011/0108025 | A1* | 5/2011 | Fink et al. ................ 128/200.16 |
| 2011/0120455 | A1 | 5/2011 | Murphy |
| 2011/0120482 | A1 | 5/2011 | Brenneise |
| 2011/0126848 | A1 | 6/2011 | Zuber et al. |
| 2011/0147486 | A1 | 6/2011 | Greim et al. |
| 2011/0150936 | A1 | 6/2011 | Villalba Gonzales et al. |
| 2011/0155153 | A1 | 6/2011 | Thorens et al. |
| 2011/0155718 | A1 | 6/2011 | Greim et al. |
| 2011/0209717 | A1 | 9/2011 | Han |
| 2011/0220134 | A1 | 9/2011 | Duke et al. |
| 2011/0226236 | A1 | 9/2011 | Buchberger |
| 2011/0232654 | A1 | 9/2011 | Mass |
| 2011/0245493 | A1 | 10/2011 | Rabinowitz et al. |
| 2011/0253798 | A1 | 10/2011 | Tucker et al. |
| 2011/0265806 | A1 | 11/2011 | Alarcon et al. |
| 2011/0277756 | A1 | 11/2011 | Terry et al. |
| 2011/0277757 | A1 | 11/2011 | Terry et al. |
| 2011/0277760 | A1 | 11/2011 | Terry et al. |
| 2011/0277761 | A1 | 11/2011 | Terry et al. |
| 2011/0277764 | A1 | 11/2011 | Terry et al. |
| 2011/0277780 | A1 | 11/2011 | Terry et al. |
| 2011/0290244 | A1 | 12/2011 | Schennum |
| 2011/0303231 | A1 | 12/2011 | Li et al. |

(56) References Cited

U.S. PATENT DOCUMENTS

| | | | | |
|---|---|---|---|---|
| 2011/0304282 | A1 | 12/2011 | Li et al. | |
| 2012/0006342 | A1 | 1/2012 | Rose et al. | |
| 2012/0006343 | A1 | 1/2012 | Renaud et al. | |
| 2012/0048266 | A1 | 3/2012 | Alelov | |
| 2012/0062041 | A1 | 3/2012 | Nelson et al. | |
| 2012/0090629 | A1 | 4/2012 | Turner et al. | |
| 2012/0090630 | A1 | 4/2012 | Hon | |
| 2012/0111347 | A1 | 5/2012 | Hon | |
| 2012/0118301 | A1 | 5/2012 | Montaser | |
| 2012/0145169 | A1 | 6/2012 | Wu | |
| 2012/0167906 | A1 | 7/2012 | Gysland | |
| 2012/0174914 | A1 | 7/2012 | Pirshafiey et al. | |
| 2012/0186593 | A1 | 7/2012 | Grano et al. | |
| 2012/0186594 | A1 | 7/2012 | Liu | |
| 2012/0199146 | A1 | 8/2012 | Marangos | |
| 2012/0199663 | A1 | 8/2012 | Qiu | |
| 2012/0211015 | A1 | 8/2012 | Li et al. | |
| 2012/0227753 | A1 | 9/2012 | Newton | |
| 2012/0230659 | A1 | 9/2012 | Goodman et al. | |
| 2012/0260927 | A1 | 10/2012 | Liu | |
| 2012/0285475 | A1 | 11/2012 | Liu | |
| 2012/0312313 | A1 | 12/2012 | Frija | |
| 2012/0318283 | A1 | 12/2012 | Watanabe et al. | |
| 2012/0318882 | A1 | 12/2012 | Abehasera | |
| 2013/0014772 | A1 | 1/2013 | Liu | |
| 2013/0019887 | A1 | 1/2013 | Liu | |
| 2013/0025609 | A1 | 1/2013 | Liu | |
| 2013/0032159 | A1 | 2/2013 | Capuano | |
| 2013/0037041 | A1 | 2/2013 | Worm et al. | |
| 2013/0042865 | A1 | 2/2013 | Monsees et al. | |
| 2013/0056013 | A1 | 3/2013 | Terry et al. | |
| 2013/0081642 | A1 | 4/2013 | Safari | |
| 2013/0118509 | A1 | 5/2013 | Richardson | |
| 2013/0183852 | A1 | 7/2013 | Rostami | |
| 2013/0192615 | A1 | 8/2013 | Tucker et al. | |
| 2013/0192616 | A1 | 8/2013 | Tucker et al. | |
| 2013/0192619 | A1 | 8/2013 | Tucker et al. | |
| 2013/0192620 | A1 | 8/2013 | Tucker et al. | |
| 2013/0192621 | A1 | 8/2013 | Li et al. | |
| 2013/0192622 | A1 | 8/2013 | Tucker et al. | |
| 2013/0192623 | A1 | 8/2013 | Tucker et al. | |
| 2013/0206154 | A1 | 8/2013 | Fernando et al. | |
| 2013/0213418 | A1 | 8/2013 | Tucker et al. | |
| 2013/0213419 | A1 | 8/2013 | Tucker et al. | |
| 2013/0220315 | A1 | 8/2013 | Conley et al. | |
| 2013/0228191 | A1 * | 9/2013 | Newton | 131/329 |
| 2013/0284192 | A1 | 10/2013 | Peleg et al. | |
| 2013/0298905 | A1 | 11/2013 | Levin et al. | |
| 2013/0300350 | A1 | 11/2013 | Xiang | |
| 2013/0306064 | A1 | 11/2013 | Thorens et al. | |
| 2013/0306065 | A1 | 11/2013 | Thorens et al. | |
| 2013/0319407 | A1 | 12/2013 | Liu | |
| 2013/0319435 | A1 | 12/2013 | Flick | |
| 2013/0319439 | A1 | 12/2013 | Gorelick et al. | |
| 2013/0319440 | A1 | 12/2013 | Capuano | |
| 2013/0340750 | A1 | 12/2013 | Thorens et al. | |
| 2013/0340775 | A1 | 12/2013 | Juster et al. | |
| 2014/0014126 | A1 | 1/2014 | Peleg et al. | |
| 2014/0034071 | A1 | 2/2014 | Levitz et al. | |
| 2014/0064715 | A1 | 3/2014 | Greim et al. | |
| 2014/0202472 | A1 | 7/2014 | Levitz et al. | |
| 2014/0261489 | A1 | 9/2014 | Cadieux et al. | |
| 2014/0261492 | A1 | 9/2014 | Kane et al. | |
| 2014/0318559 | A1 | 10/2014 | Thorens et al. | |

FOREIGN PATENT DOCUMENTS

| | | | |
|---|---|---|---|
| CH | 421786 | | 9/1966 |
| CN | 87104459 | A | 2/1988 |
| CN | 1040914 | | 4/1990 |
| CN | 2719043 | | 8/2005 |
| CN | 2777995 | Y | 5/2006 |
| CN | 2887086 | | 4/2007 |
| CN | 200983833 | | 12/2007 |
| CN | 101116542 | | 2/2008 |
| CN | 201018927 | | 2/2008 |
| CN | 201029436 | | 3/2008 |
| CN | 201051762 | | 4/2008 |
| CN | 201054977 | | 5/2008 |
| CN | 201067079 | | 6/2008 |
| CN | 201076006 | | 6/2008 |
| CN | 201085044 | | 7/2008 |
| CN | 101322579 | A | 12/2008 |
| CN | 101371721 | | 2/2009 |
| CN | 101518361 | | 9/2009 |
| CN | 201379072 | | 1/2010 |
| CN | 201571500 | | 9/2010 |
| CN | 201709398 | U | 1/2011 |
| CN | 201789924 | U | 4/2011 |
| CN | 201797997 | U | 4/2011 |
| CN | 102106611 | A | 6/2011 |
| CN | 201860753 | U | 6/2011 |
| CN | 102166044 | A | 8/2011 |
| CN | 201986689 | | 9/2011 |
| CN | 202014571 | U | 10/2011 |
| CN | 202014572 | U | 10/2011 |
| CN | 202026802 | | 11/2011 |
| CN | 202026804 | U | 11/2011 |
| CN | 202233005 | U | 5/2012 |
| CN | 202233007 | U | 5/2012 |
| DE | 1632249 | | 12/1970 |
| DE | 2547941 | | 4/1977 |
| DE | 3006553 | | 4/1977 |
| DE | 3640917 | | 8/1988 |
| DE | 3735704 | | 5/1989 |
| DE | 19854009 | | 5/2000 |
| DE | 69824982 | | 10/2004 |
| EP | 0057243 | | 8/1982 |
| EP | 0086180 | | 8/1983 |
| EP | 0117355 | | 9/1984 |
| EP | 0236992 | | 9/1987 |
| EP | 0277519 | | 8/1988 |
| EP | 0295122 | | 12/1988 |
| EP | 0358 002 | | 3/1990 |
| EP | 0358114 | | 3/1990 |
| EP | 0430566 | | 5/1990 |
| EP | 0438862 | | 7/1991 |
| EP | 0488488 | | 6/1992 |
| EP | 0503767 | | 9/1992 |
| EP | 0608783 | | 3/1994 |
| EP | 0845220 | | 6/1998 |
| EP | 0857431 | | 8/1998 |
| EP | 0893071 | | 1/1999 |
| EP | 1298808 | | 4/2003 |
| EP | 1618803 | | 1/2006 |
| EP | 1736065 | | 12/2006 |
| EP | 2113178 | | 4/2008 |
| EP | 1989946 | | 11/2008 |
| EP | 2022350 | | 2/2009 |
| EP | 2110033 | | 10/2009 |
| EP | 2481308 | | 8/2012 |
| GB | 1397351 | | 6/1975 |
| GB | 1528391 | | 10/1978 |
| GB | 2089188 | | 6/1982 |
| GB | 2115676 | | 9/1983 |
| GB | 2132539 | | 7/1984 |
| GB | 2148079 | | 5/1985 |
| GB | 2148676 | | 5/1985 |
| JP | 61068061 | | 4/1986 |
| JP | 2006320286 | | 11/2006 |
| JP | 2010-213579 | | 9/2010 |
| KR | 100636287 | | 10/2006 |
| NL | 8201585 | | 11/1982 |
| WO | WO86/02528 | | 5/1986 |
| WO | WO9003224 | | 4/1990 |
| WO | WO95/02970 | | 2/1995 |
| WO | WO98/43019 | | 10/1998 |
| WO | WO00/28843 | | 3/2000 |
| WO | WO00/28843 | | 5/2000 |
| WO | WO03037412 | | 5/2003 |
| WO | W 03/095688 | | 11/2003 |
| WO | WO2004/043175 | | 5/2004 |
| WO | WO2004/080216 | | 9/2004 |

(56) References Cited

FOREIGN PATENT DOCUMENTS

| | | |
|---|---|---|
| WO | WO2004/095955 | 11/2004 |
| WO | WO2005/099494 | 10/2005 |
| WO | WO2005120614 | 12/2005 |
| WO | WO2007024130 | 3/2007 |
| WO | WO2007/066374 | 6/2007 |
| WO | WO2007/078273 | 7/2007 |
| WO | WO2007/098337 | 8/2007 |
| WO | WO2007/131449 | 11/2007 |
| WO | WO2007/131450 | 11/2007 |
| WO | WO2007/141668 | 12/2007 |
| WO | WO2008/055423 | 5/2008 |
| WO | WO2010/091593 | 8/2010 |
| WO | WO2010/145468 | 12/2010 |
| WO | WO2011/121326 | 10/2011 |
| WO | WO2011/124033 | 10/2011 |
| WO | WO2011/125058 | 10/2011 |
| WO | WO2011/146372 | 11/2011 |
| WO | WO2012/088675 | 7/2012 |
| WO | WO2012/109371 | 8/2012 |
| WO | WO2012/129787 | 10/2012 |
| WO | WO2012/129812 | 10/2012 |
| WO | WO2012/142293 | 10/2012 |
| WO | WO2013/093695 | 6/2013 |
| WO | WO2013/116558 | 8/2013 |

OTHER PUBLICATIONS

International Search Report and Written Opinion for PCT/US13/24211 dated Apr. 19, 2013.
International Search Report and Written Opinion for PCT/US13/24219 dated Apr. 22, 2013.
International Search Report and Written Opinion for PCT/US13/24229 dated Apr. 22, 2013.
International Search Report and Written Opinion for PCT/US13/24215 dated Apr. 22, 2013.
International Search Report and Written Opinion for PCT/US13/24222 dated Apr. 24, 2013.
International Search Report and Written Opinion for PCT/US13/27424 dated Apr. 25, 2013.
International Search Report and Written Opinion for PCT/US13/27432 dated May 2, 2013.
International Search Report and Written Opinion for PCT/US13/24224 dated May 13, 2013.
U.S. Appl. No. 13/843,028, filed Mar. 15, 2013, to Fath et al.
U.S. Appl. No. 13/843,314, filed Mar. 15, 2013, to Fath et al.
U.S. Appl. No. 13/843,449, filed Mar. 15, 2013, to Fath et al.
Excerpt from "NASA Tech Briefs", Jul./Aug. 1988, p. 31.
RjG, Comment to Exactly What Material Is the Wick?, E-Cigarette Forum (Jan. 2, 2010, 9:27 PM), http://www.e-cigarette-forum.com/forum/atomizer-mods/58918-exactly-what-material-wick.html.
International Search Report and Written Opinion for PCT/US2012/033329 dated Oct. 4, 2012.
International Preliminary Report on Patentability for PCT/US2012/033329 dated Oct. 15, 2013.
International Preliminary Report on Patentability for PCT/US2013/024215 dated Aug. 14, 2014.
International Preliminary Report on Patentability for PCT/US2013/024219 dated Aug. 14, 2014.
International Preliminary Report on Patentability for PCT/US2013/024229 dated Aug. 14, 2014.
European Search Report for EP 08251579.2 dated Nov. 7, 2008.
European Search Report for EP 09252490 dated Mar. 11, 2010.
International Search Report and Written Opinion for PCT/EP2010/006534 dated Apr. 5, 2011.
International Preliminary Report on Patentability for PCT/EP2010/006534 dated May 10, 2012.
U.S. Appl. No. 14/332,785, filed Jul. 16, 2014, to Janardhan et al.
U.S. Appl. No. 14/337,872, filed Jul. 22, 2014, to Janardhan et al.
U.S. Appl. No. 14/337,353, filed Jul. 22, 2014, to Janardhan et al.
U.S. Appl. No. 29/456,109, filed May 29, 2013, to Weigensberg.
U.S. Appl. No. 29/469,749, filed Oct. 14, 2013, to Tucker et al.
U.S. Appl. No. 29/473,662, filed Nov. 25, 2013, to Tucker et al.
U.S. Appl. No. 29/469,741, filed Oct. 14, 2013, to Tucker et al.
U.S. Appl. No. 29/469,750, filed Oct. 14, 2013, to Tucker et al.
U.S. Appl. No. 29/471,338, filed Oct. 30, 2013, to Bramley et al.
U.S. Appl. No. 29/471,454, filed Oct. 31, 2013, to Bramley et al.
U.S. Appl. No. 29/503,697, filed Sep. 29, 2014, to Bramley et al.
"Joining of Ceramics" by R.E. Loehman et al., published in Ceramic Bulletin, 67(d); 375-380 (1988).
Oxidation Behavior of Silver—and Copper-Based Brazing Filler Metals for Silicon Nitride/Metal Joints by R.R. Kapoor et al., published in J. Am. Ceram. Soc., 72(3):448-454 (1989).
"Brazing Ceramic Oxides to Metals at Low Temperatures" by J.P. Hammond et al., published in Welding Research Supplement, 227-232-s, (1988).
"Brazing of Titanium-Vapor-Coated Silicon Nitride" by M. L. Santella, published in Advanced Ceramic Materials, 3(5):457-465 (1988).
"High Temperature Structural Silicides" by A.K. Vasudevan et al., Elsevier Science Publishers B.V. (1992).
John A. Dean, Lange's handbook of Chemistry, 12th Edition, 1978 pp. 4-16, 4-123.
Fen et al., "Cyclic oxidation of Haynes 230 alloy", Chapman & Hall, pp. 1514-1520 (1992).
Reinshagen and Sikka, "Thermal Spraying of Selected Aluminides", Proceedings of the Fourth National Thermal Spray Conference, Pittsburgh, PA USA, pp. 307-313 (May 4-10, 1991).
Kutner, "Thermal spray by design", Reprint from Advanced Materials & Processes Incorporating Metal Progress, Oct. 1988.
"Characterizing Thermal Spray Coatings", Article based on presentation made at the Fourth National Thermal Spray Conference, May 4-10, 1991 and appearing in Advanced Materials and Processes, May 1992, pp. 23-27.
Howes, Jr., "Computerized Plasma Control for Applying Medical-Quality Coatings", Industrial Healing, pp. 22-25, Aug. 1993.
V. Sikka, "Processing of Aluminides", Intermetallic Metallurgy and Processing Intermetallic Compounds, ed Stoloff et al., Van Mestrand Reinhold, N.Y., 1994.
K.H. Jack, "The Iron-Nitrogen System: The Crystal Structures of ∈-Phase Iron Nitrides", Aceta Crystallographica, 5. pp. 404-411 (1952).
K.H. Jack, "Binary and ternary interstitial alloys 1. The iron-nitrogen system: the structures of Fe4N and Fe2N", Proceedings of the Royal Society, A. 195, pp. 34-40 (1948).
K.H. Jack, "The iron-nitrogen system: the preparation and the crystal structures of nitrogen-austenite (Y) and nitrogen-martensite (a)", Proceedings of the Royal Society, A. 208, pp. 200-215 (1952).

* cited by examiner

ELECTRONIC SMOKING ARTICLE

CROSS REFERENCE TO RELATED APPLICATION

This application claims priority under 35 U.S.C. §119(e) to U.S. Provisional Application No. 61/593,004, filed on Jan. 31, 2012, the entire content of which is incorporated herein by reference thereto.

SUMMARY OF SELECTED FEATURES

An electronic cigarette or cigar (collectively "electronic smoking article") is provided which includes a heater element which vaporizes liquid material to produce an aerosol or "vapor". In an embodiment, the heater element comprises a resistive heater coil, with a wick extending therethrough. Aerosol generated by the heater coil and wick assembly is drawn down a central channel toward the mouth end portion of the smoking article.

The electronic article preferably includes a mechanical aerosol converter (MAC) insert having a face and one or more outlets. The face and outlets of the MAC insert are mutually arranged and the face is aligned with the central channel so as to cause the aerosol to strike the face prior to it being drawn out from the article. As a result, the aerosol particle size distribution is shifted to a distribution comprising a range of smaller particles, and both the vapor phase components of the aerosol and the temperature of the aerosol are reduced. These effects and possibly others are believed to contribute to sensory attributes of reduced throat irritation, even at higher levels of nicotine content in the liquid formulation, and to improved mouth feel over aerosols of electronic smoking articles lacking a MAC insert as taught herein.

DETAILED DESCRIPTION

Electronic Smoking Article Layout

Figure 1A:
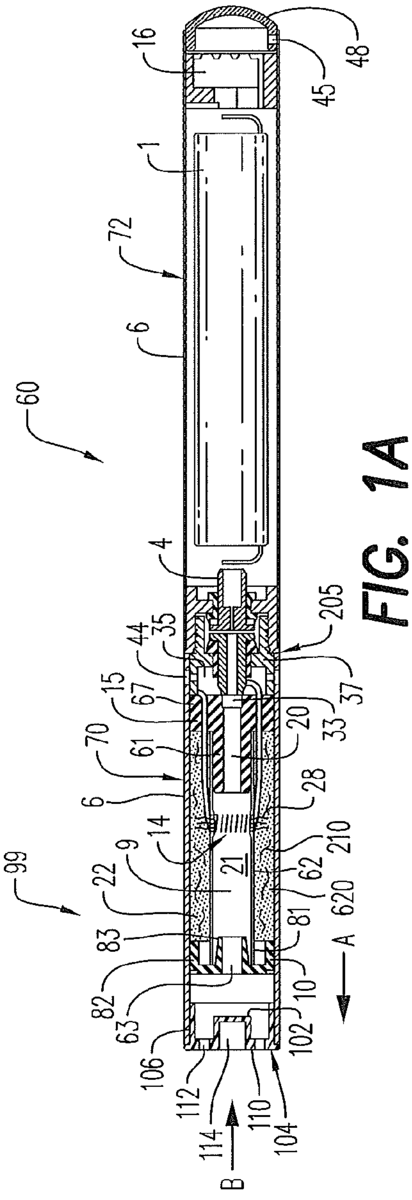
FIGS. 1A and 1B are cross sectional side views of an electronic smoking article according to a first embodiment.
Figure 1B:
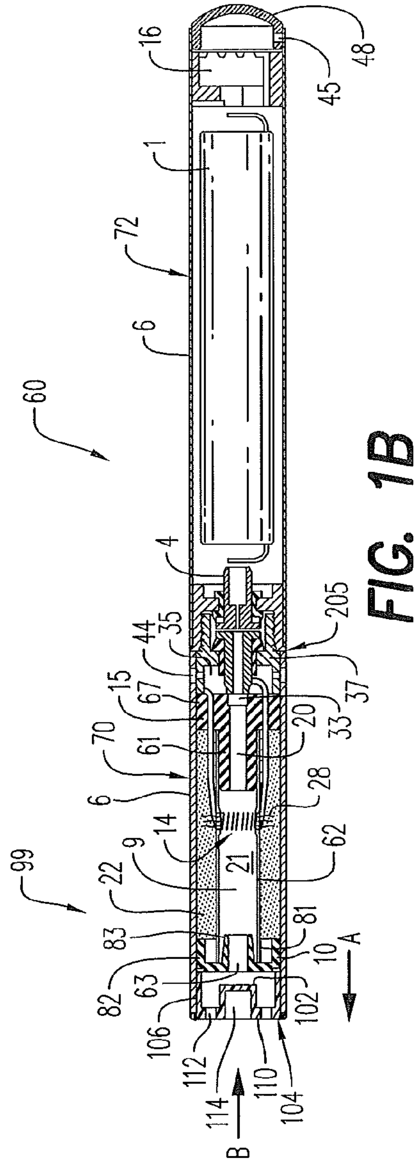

Referring to FIGS. 1A and 1B, an electronic smoking article (cigarette) 60 comprises a replaceable cartridge (or first section) 70 and a reusable fixture (or second section) 72, which in the preferred embodiment, are coupled together at a threaded connection 205 or by other convenience such as a snug-fit, detent, snap-fit, clamp and/or clasp. Generally, the second section 72 includes a puff sensor 16 responsive to air drawn into the second section 72 via an air inlet port 45 adjacent the free end or tip of the electronic smoking article 60, a battery 1 and control circuitry. The disposable first section 70 includes a liquid supply region 22 of liquid and a heater 14 that aerosolizes liquid that is drawn from the liquid supply region 22 through a wick 28. Upon completing the threaded connection 205, the battery 1 is connectable with the electrical heater 14 of the first section 70 upon actuation of the puff sensor. Air is drawn primarily into the first section 70 through one or more air inlets 44 located in the outer tube (casing) 6.

In a preferred embodiment, once the liquid of the cartridge is spent, only the first section 70 is replaced. An alternate arrangement includes a layout where the entire electronic smoking article 60 is disposed once the liquid supply is depleted. In such case the battery type and other features might be engineered for simplicity and cost-effectiveness, but generally embodies the same concepts as in the preferred embodiment in which the second section is reused and/or recharged.

In a preferred embodiment, the electronic smoking article 60 is about the same size as a conventional cigarette. In some embodiments, the electronic smoking article 60 can be about 80 mm to about 110 mm long, preferably about 80 mm to about 100 mm long and about 7 mm to about 8 mm in diameter. For example, in a preferred embodiment, the electronic smoking article is about 84 mm long and has a diameter of about 7.8 mm.

Preferably, at least one adhesive-backed label is applied to the outer tube 6, preferably about the first section 70. The label preferably completely circumscribes the electronic smoking article 60 and can be colored and/or textured to provide the look and/or feel of a traditional cigarette. The label can include holes therein which are sized and positioned so as to prevent blocking of the air inlets 44 in the outer tube 6 (or casing).

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. Preferably, the material is light and non-brittle. The inner tube 62 can also include a substantially water impermeable coating.

Referring now to FIGS. 1A, 1B, 6 and 9, the first section 70 includes the outer tube (or casing) 6 extending in a longitudinal direction and the inner tube (or chimney) 62 coaxially positioned within the outer tube 6. Preferably, a nose portion 61 of an upstream gasket (or seal) 15 is fitted into an upstream end portion 65 of the inner tube 62, while at the same time, an outer perimeter 67 of the upstream gasket 15 provides a liquid-tight seal with an interior surface of the outer tube 6. The upstream gasket 15 also includes a central, longitudinal air passage 20, which opens into an interior of the inner tube 62 that defines a central channel 21.

Referring to FIG. 1, a transverse channel 33 can be provided across a backside potion of the upstream gasket 15, which intersects and communicates with the central channel 20 of the gasket 15. This channel 33 assures communication between the central channel 20 and a space 35 defined within a cathode connector piece 37. In the preferred embodiment, the piece 37 includes a threaded section for effecting the threaded connection 205. The cathode connector piece 37 includes opposing notches about its perimeter, which, upon insertion of the cathode connector piece 37 into the outer tube 6, are aligned with the location of each of two RTD-controlling, air inlet ports 44 and 44' in the outer tube 6. Preferably, the air inlet ports 44 and 44' are precision drilled so as to provide the smoking article a predetermined, desired resistance to draw (RTD) ranging from about 60 mm $H_2O$ to about 150 mm $H_2O$, more preferably about 90 mm $H_2O$ to about 110 mm $H_2O$, most preferably about 100 mm $H_2O$ to about 130 mm $H_2O$.

The space defined between the upstream gasket 15, a downstream gasket 10 and the outer tube 6 and the inner tube 62 establish the confines of the liquid supply region 22. The liquid supply region 22 comprises a liquid material and optionally a liquid storage medium 210 operable to store the liquid material therein. The liquid storage medium 210 may comprise a winding of cotton gauze or other fibrous material about the inner tube 62.

In the preferred embodiment, the liquid supply region 22 is contained in an outer annulus 620 between inner tube 62 and outer tube 6 and between the gaskets 10 and 15. Thus, the liquid supply region 22 at least partially surrounds the central air passage 21. The heater 14 preferably extends transversely across the central channel 21 between opposing portions of the liquid supply region 22, although the teachings herein are applicable to arrangements wherein the heater 14 is oriented in the longitudinal direction instead of transversely.

Preferably, the liquid storage medium 210 is a fibrous material comprising cotton, polyethylene, polyester, rayon and combinations thereof. Preferably, the fibers have a diameter ranging in size from about 6 microns to about 15 microns (e.g., about 8 microns to about 12 microns or about 9 microns to about 11 microns). The liquid storage medium 210 can be a sintered, porous or foamed material. Also preferably, the fibers are sized to be irrespirable and can have a cross-section which has a y shape, cross shape, clover shape or any other suitable shape. In the alternative, the liquid supply region 22 may comprise a filled tank lacking a fibrous storage medium 21 and containing only liquid material.

Also preferably, the liquid material has a boiling point suitable for use in the electronic smoking article 60. If the boiling point is too high, the heater 14 will not be able to vaporize liquid in the wick 28. However, if the boiling point is too low, the liquid may vaporize even when the heater 14 is not being activated.

Preferably, the liquid material includes a tobacco-containing material including volatile tobacco flavor compounds which are released from the liquid upon heating. The liquid may also be a tobacco flavor containing material or a nicotine-containing material. Alternatively, or in addition, the liquid may include a non-tobacco material. For example, the liquid may include water, solvents, ethanol, plant extracts and natural or artificial flavors. Preferably, the liquid further includes an aerosol former. Examples of suitable aerosol formers are glycerine and propylene glycol.

In use, liquid material is transferred from the liquid supply region 22 and/or liquid storage medium 210 by capillary action at each end portion of the wick 28. In an embodiment, the heater 14 can at least partially surround a central portion of the wick 28 such that when the heater 14 is activated, the liquid in that portion of the wick 28 is vaporized by the heater 14 to form an aerosol. In other embodiments, the heater 14 can be disposed adjacent a portion of the wick without being wound about the wick. The wick 28 preferably comprises filaments having a capacity to draw a liquid, more preferably a bundle of glass (or ceramic) filaments and most preferably a bundle comprising a group of windings of glass filaments, preferably three of such windings, all which arrangements are capable of drawing liquid via capillary action via spacings between the filaments. Preferably, the wick 28 is flexible and includes three strands, each strand including a plurality of filaments. Moreover, it is noted that the end portions of the wick 28 are preferably flexible and foldable into the confines of the liquid supply region 22.

Preferably, a nose portion 81 of a downstream gasket 10 is fitted into a downstream end portion 83 of the inner tube 62. An outer perimeter 82 of the gasket 10 provides a substantially liquid-tight seal with an interior surface of the outer tube 6. Aerosol generated by the heater 14 travels from the central channel 21 and through a central channel 63 in the downstream gasket 10 and into a remaining downstream end portion of a mouth piece portion 99 of the smoking article 60. From the central channel 63 of the gasket 10, the aerosol, in substantial part, is drawn into contact with a face 102 of a mechanical aerosol converter (MAC) insert 104.

Figure 2:
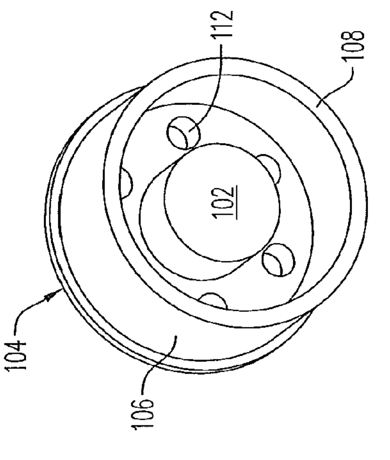
FIG. 2 is a perspective view of a mechanical aerosol converter (MAC) insert of the electronic smoking article shown in FIG. 1A, the perspective being viewed in the general direction of arrow A in FIG. 1A.

Referring now to FIG. 2, in one embodiment, the MAC insert 104 comprises a cylindrical body portion 106 having an outer diameter that can be sized to provide a sliding fit with the interior surfaces of the outer tube 6 of the smoking article 60. As shown in FIG. 1B, an upstream end portion 108 of the cylindrical body portion 106 of the MAC insert 104 is preferably brought into contact with adjacent portions of the gasket 10 so that the spatial relationship and orientation between the MAC insert 104 and the gasket 10 are essentially the same from one article 60 to the next. Thus, the body portion 106 is provided with a length such that a face portion 110 of the MAC insert 104 is flush with or at some other desired relation with the downstream end of the outer tube 6. The MAC insert 104 can be formed of any suitable substantially air impermeable material, such as plastic or metal foil.

The transverse, annular face portion 110 of the MAC insert 104 is provided with a plurality of orifices 112, which in an embodiment comprise six circular orifices 112, each orifice having a diameter ranging from about 0.015 inch to about 0.090 inch (e.g., about 0.020 inch to about 0.040 inch or about 0.028 inch to about 0.038 inch). After contacting the face 102 of the MAC insert 104, aerosol is then drawn through the orifices 112 in the MAC insert 104, which are disposed radially about the face 102.

Although the orifices 112 are shown as extending in a longitudinal direction, all or some of them may be directed divergently so as to impart a radially outward component to the velocity to the aerosol streams as they are drawn through the MAC insert 104. The number, size and shape of the orifices can be varied in the practice of the teachings herein.

Figure 4:
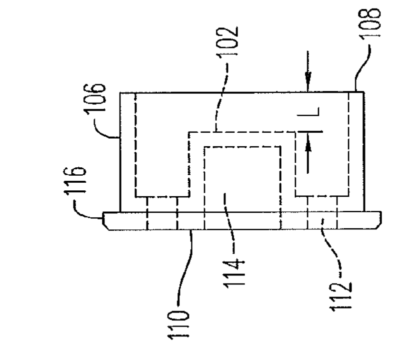
FIG. 4 is a side view of the MAC insert of FIGS. 1A, 2 and 3A, with interior features of the face shown in dashed lines.

Referring now to FIGS. 2 and 4, the face 102 of the MAC insert 104 is disposed within the confines of the cylindrical body portion 106 by a predetermined spacing "L" from the edge portion 108 of the cylindrical body portion 106 such that upon placement of the MAC insert 104 against the gasket 10, the face 102 is positioned a predetermined distance apart from the discharge orifice 63 of the gasket 10. In a preferred embodiment, that distance is in the range of about 1 mm to about 3 mm, more preferably in the range of about 1.5 mm to about 2.5 mm, but could be established at other values through analytic testing and/or modeling to find which distance is preferred for any particular design of the electronic smoking article 60.

Figure 3A:
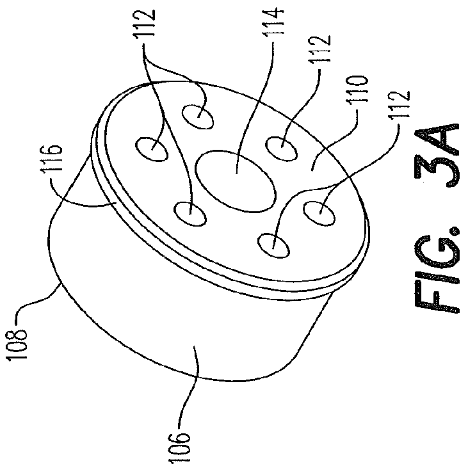
FIGS. 3A and 3B are perspective views of MAC inserts of FIGS. 1A and 1B, the perspective being viewed in the general direction of arrow B in FIGS. 1A and 1B.
Figure 3B:
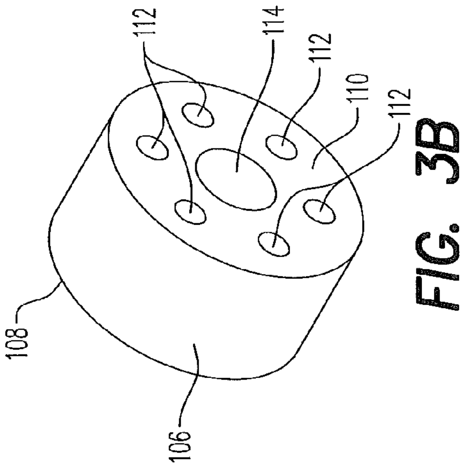

Referring to FIGS. 3A, 3B, and 4, the MAC insert 104 can include a central recess 114 to facilitate molding operations during the manufacture of the MAC insert 104. It is envisioned that the MAC insert 104 could be formed without the recess 114 such that an external face portion 110 of the insert is generally circular and planar instead of being annular as shown in FIGS. 3A and 3B. In addition, the MAC insert 104 may be provided with a flange 116 (as shown in FIG. 3A) which could act as a stop against the downstream edge of the outer tube 6 so as to register placement within the smoking article 60 with the flange 116 instead of abutment against the insert 10 as shown in FIG. 1A. Such arrangement is advantageous when it is desired to locate the MAC insert 104 in spaced apart relation from the gasket 10. It is also envisioned that the MAC insert 104 and the gasket 10 can be integrally formed so as to simplify manufacture and assembly of the electronic smoking article 60.

Figure 8:
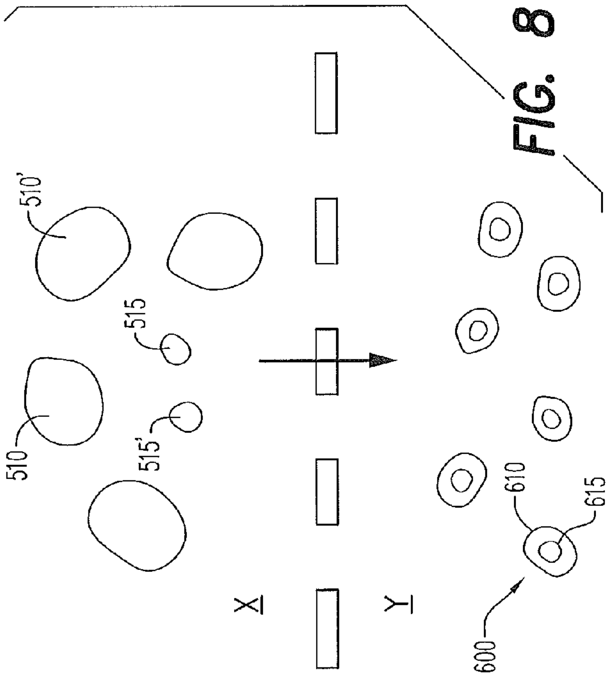
FIG. 8 is a stylized representation of a possible effect of aerosol striking a MAC insert prior to exiting an electronic smoking.

Referring now to FIGS. 1 and 8, as aerosol is drawn through the central channel 63 of the gasket 10, it is directed against the face 102 of the MAC insert 104, whereupon heat is exchanged such that the temperature of the aerosol is reduced. In some cases, the temperature can be reduced by 30° C. or more. When the aerosol strikes the face 102, larger aerosol particles, as represented in region X of FIG. 8, tend to break up to form several smaller particles, as represented in region Y.

In particular and in reference to region X of FIG. 8, it is believed for that upon exiting the central channel 63 of the gasket 10, the aerosol comprises large particles of propylene glycol and water 510 and relatively large, separate particles of nicotine droplets 515. The relatively large, nicotine droplets 515 comprise a vapor phase component of the aerosol and are known to contribute undesirable sensory responses such as throat irritation and/or harshness when inhaled.

Not wishing to be bound by theory, upon striking the face 102 of the MAC insert 104, it is believed that the aerosol undergoes a transformation such as shown in region Y of FIG. 8, whereby larger particles 510 and 515 of the aerosol as previously described become smaller particulate phase constituents 600 comprising smaller, particulate phase nicotine 615 surrounded by propylene glycol 610.

As a result of drawing the aerosol through the MAC insert 104, it has been found that the aerosol of the electronic smoking article 60 tends to be lower in temperature, to have a particle size distribution that has shifted toward a range of smaller particle sizes and that the vapor phase components as previously described are reduced. It is also believed that the MAC insert 104 increases production of core-shell particles comprising a nicotine particle surrounded by a shell of propylene glycol. These attributes and others are believed to contribute to a finding that the aerosol has acceptable sensory attributes including less throat irritation and improved sensory experience, even at higher nicotine levels in the liquid formulation. The reduced aerosol temperature is believed to improve mouth feel.

As noted, use of the MAC insert 104 tends to avoid perceived sensory deficits when elevated levels of nicotine are added to the liquid formulation of an electronic smoking article. For example, an electronic smoking article of the prior art tends to produce perceived sensations of harshness and/or irritation if the liquid formulation is modified to include nicotine at levels greater than 2% by weight. It has been found that with inclusion of a MAC insert in accordance with the teachings herein, nicotine levels in the liquid formulation can be increased up to 6% nicotine with acceptable sensory attributes. Such provides opportunity to produce an electronic smoking article 60 having high impact with little to no irritation. With inclusion of the MAC insert 104, an electronic smoking article can be constructed which provides 0.18 mg of nicotine per puff on a 10 puff basis, which provides comparable levels of nicotine when compared to traditional cigarettes, with acceptable sensory attributes.

With regard to particle size distribution, it has been found that particles size distribution of an aerosol from a smoking article lacking a MAC insert as taught herein has a bell-shaped distribution of sizes in the range of about 0.1 nanometer (nm) to about 0.7 nm. In contrast, the particles size distribution of an aerosol from an electronic smoking article including the MAC insert as described herein has a bell-shaped distribution of sizes in the range of about 0.1 nm to about 0.6 nm, a significant decrease in particle size distribution.

It has also been found that some electronic smoking articles not including a MAC insert tend to produce aerosols having temperatures at or above 110° Celsius. In contrast, an electronic smoking article 60 as described in FIGS. 1A and 1B, which include the MAC insert 104, produce an aerosol having a temperature, when measured at the exit of the mouth end of the electronic smoking article 60, of about 60° C. to about 100° C.

Figure 5A:
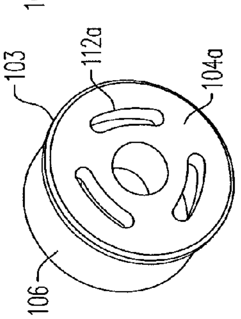
FIG. 5A is a perspective view of an another embodiment of a MAC insert including a flange for use in the electronic smoking article shown in FIG. 1A, the perspective being viewed in the general direction of arrow B in FIG. 1A.

Referring now to FIG. 5A, according to another embodiment, the MAC insert 104*a*, 104*b* includes three exit orifices 112*a*, 112*b* that are elongated, generally kidney shaped and extend circumferentially about the perimeter of the face 102*a*, 102*b* of the MAC insert 104*a*, 104*b*. Being larger, the orifices 112*a*, 112*b* are less subject to risk of accumulation of material and blockage. In a preferred embodiment, each orifice 112*a*, 112*b* has a length of about 2 mm to about 5 mm, preferably about 3 mm to about 4 mm, and a width of about 0.5 mm to about 1 mm in width. The face 102*a*, 102*b* can have a diameter of about 3 mm to about 5 mm. The size, circumferential extent and the number of the orifices 112*a*, 112*b* may be varied in the practice of these teachings with respect to any particular article.

Figure 6:
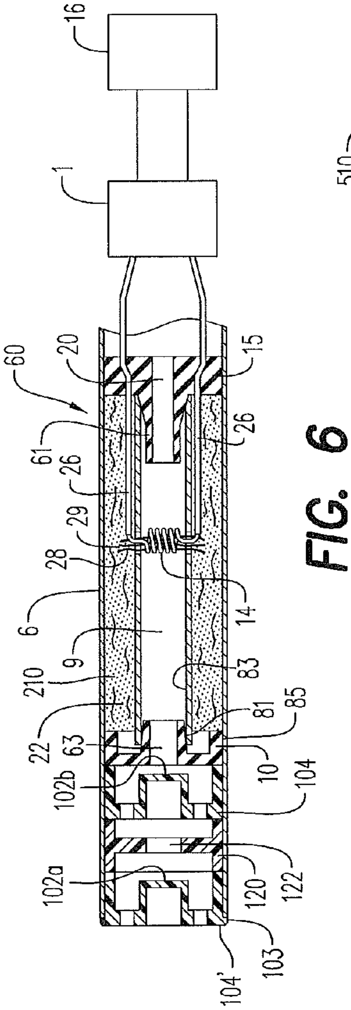
FIG. 6 is an abbreviated sectional side view of an electronic smoking article in accordance with another embodiment including a flow-centralizer disc interposed between a first MAC insert, shown in FIG. 5A, and a second MAC insert, shown in FIG. 5B.

Referring now to FIG. 6, another embodiment of an electronic smoking article 60 comprises many of the same components as described with reference to FIGS. 1A and 1B, but with the battery section 1 and the puff sensors/control circuitry 16 shown in block diagram. In this embodiment, a first MAC insert 104*b* is disposed immediately downstream of the gasket 10 as previously described with reference to FIG. 1. A disk 120 having a central orifice 122 is positioned downstream of the first MAC insert 104*b* and immediately upstream of a second MAC insert 104*a*.

The disc 122 with its central orifice 122 operates to centralize the discharge of the first MAC insert 104*b* before it is drawn through the second MAC insert 104*a*. In essence the flow-centralizing disc imparts additional compaction of the aerosol while also directing the flow against the face 102*a* of the second MAC insert 104*a*. With this arrangement, additional mechanical aerosol converting events are imparted on the aerosol so as to further enhance the beneficial aspects of reduction of aerosol particle size upon the aerosol generated by the electronic smoking article 60.

Figure 5B:
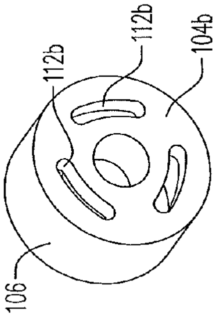
FIG. 5B is a perspective view of an another embodiment of a MAC insert excluding a flange for use in the electronic smoking article shown in FIG. 1B, the perspective being viewed in the general direction of arrow B in FIG. 1B.
Figure 7:
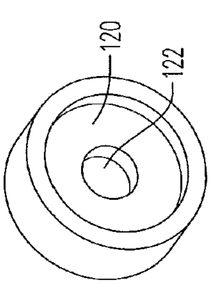
FIG. 7 is a perspective view of the flow-centralizing disc of FIG. 6.

It is envisioned that the first MAC insert 104*b* may have orifices of the shape such as shown in FIG. 2, whereas the second MAC insert 104*a* might have the elongated orifices shown in FIG. 5A or 5B or vise-versa. Alternatively, both the first MAC insert 104*b* and the second MAC insert 104*a* can include the round orifices shown in FIGS. 2 and 3 or both can include the elongated orifices shown in FIGS. 5A and 5B. Moreover, the second MAC insert 104*a* can include a flange 103 as shown in FIG. 5A, while the first MAC insert 104*b* may exclude a flange.

Figure 9:
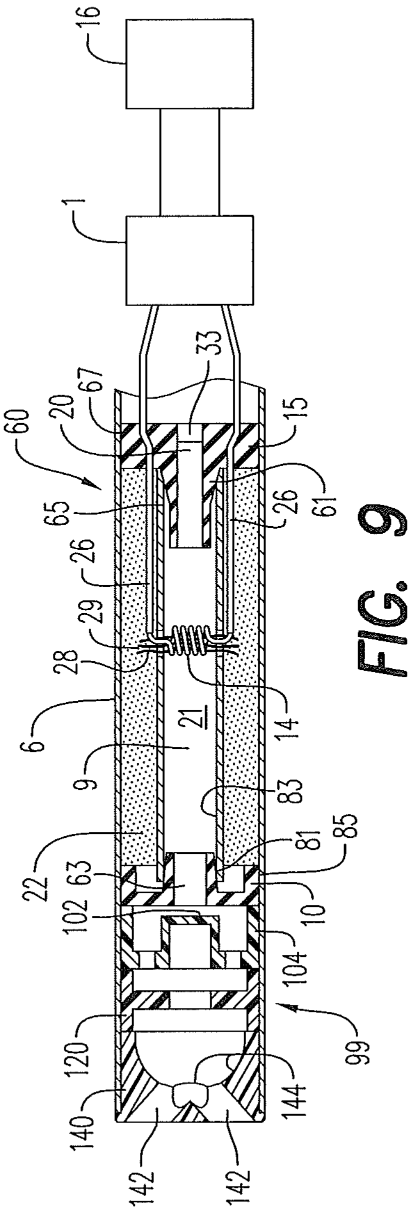
FIG. 9 is an abbreviated sectional side view of an electronic smoking article having a mouth end insert constructed in accordance with another embodiment, and including a flow-centralizer disc interposed between an upstream MAC insert, as shown in FIG. 5B, and a downstream, multi-ported mouthpiece insert.

Referring now to FIG. 9, another embodiment provides a smoking article as previously described including a downstream gasket 10 followed by (in the sense of direction of aerosol flow), a MAC insert 104, 104*a*, 104*b*, as shown in FIG. 2, 5A or 5B, which is in turn is followed by a disk 120, as previously described, which in turn is followed by a multiport mouth end insert 140 having a plurality of divergent passages 142. Referring now also to FIG. 10A, the multi-port mouth end insert 140 is constructed in accordance with the teachings of U.S. application Ser. No. 13/741,217 to Tucker et al. filed Jan. 14, 2013 and titled "Electronic Cigarette", which is incorporated in its entirety by reference thereto.

In a preferred embodiment, the multi-port mouth end insert 140 includes at least two diverging outlet passages 142 (e.g., preferably 2 to 10 outlet passages 142, more preferably 4 outlet passages or 3, 4, 5, 6, or more passages 142). Preferably, the outlet passages 142 are located off-axis and are angled outwardly in relation to the central channel 21 of the inner tube 62 (i.e., divergently). Also preferably, the outlets 142 are uniformly distributed about a perimeter of the insert 140 so as to substantially uniformly distribute aerosol in a smoker's mouth during use and create a greater perception of fullness in the mouth. Thus, as the aerosol passes into a smoker's mouth, the aerosol enters the mouth and moves in divergent directions so as to provide a full mouth feel. In contrast, electronic smoking articles having a single, on-axis orifice tend to direct its aerosol as single jet of greater velocity toward a more limited location within a smoker's mouth.

In addition, the multi-ported mouthpiece insert 140 and its diverging outlet passages 142 are arranged and include interior surfaces 144 such that droplets of un-aerosolized liquid material, if any, that may be entrained in the aerosol strike the interior surfaces 144 of the mouth end insert 140 and/or strike portions of walls of the diverging outlet passages 142. As a result such droplets are substantially removed or broken apart so as to enhance o\the aerosol.

In the preferred embodiment, the diverging outlet passages 142 are angled at about 5° to about 60° with respect to the longitudinal axis of the outer tube 6 so as to more completely distribute aerosol throughout a mouth of a smoker during use and to remove droplets. In a preferred embodiment, there are four diverging outlet passages 142, each at an angle of about 40° to about 50° with respect to the longitudinal axis of the outer tube 6, more preferably about 40° to about 45° and most preferably about 42°.

Preferably, each of the diverging outlet passages 142 has a diameter ranging from about 0.015 inch to about 0.090 inch (e.g., about 0.020 inch to about 0.040 inch or about 0.028 inch to about 0.038 inch). The size of the diverging outlet passages 24 and the number of diverging outlet passages 24 can be selected to adjust the resistance to draw (RTD) of the electronic smoking article 60, if desired. Moreover, the mouth end insert 8 can be formed of a polymer selected from the group consisting of low density polyethylene, high density polyethylene, polypropylene, polyvinylchloride, polyetheretherketone (PEEK) and combinations thereof. The mouth end insert 8 may also be colored if desired.

Figure 10B:
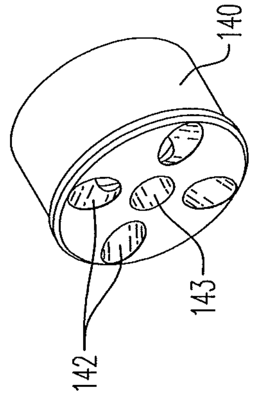
FIGS. 10A and 10B are perspective views of a multi-ported mouth end insert for use in the electronic smoking article of FIG. 9.
Figure 10A:
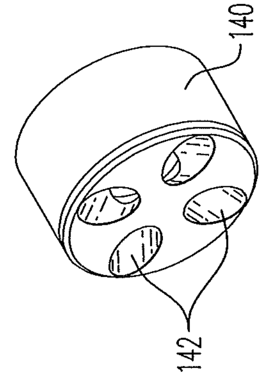

In one embodiment, shown in FIG. 10B, the mouth end insert 140 can include an on-axis central outlet passage 143, together with the diverging outlet passages 142.

As shown in FIG. 9, an interior surface 144 of the mouth end insert 140 can comprise a generally domed surface 144. Alternatively, the interior surface 144 of the mouth end insert 140 can be generally cylindrical or frustoconical, with a planar end surface. Preferably, the interior surface 144 is substantially uniform over the surface thereof. Moreover, the interior surface 144 can be symmetrical about the longitudinal axis of the mouth end insert 140. However, in other embodiments, the interior surface 140 can be irregular and/or have other shapes.

In a preferred embodiment, the interior surfaces 144 of the insert 140 may include a void disposed at the convergence of the diverging outlet passages 144.

Figure 11:
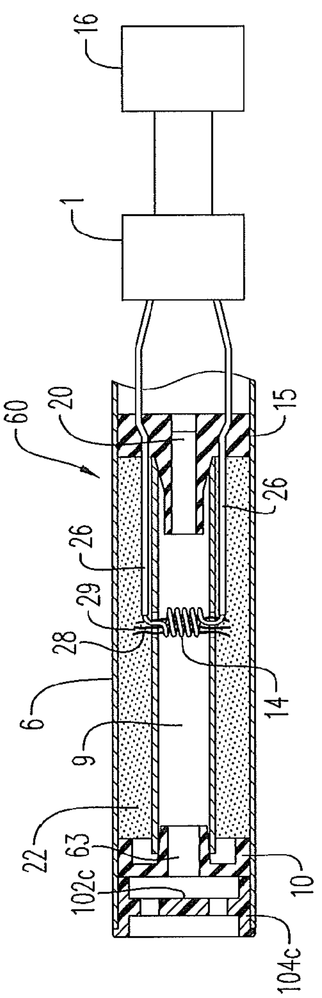
FIG. 11 is an abbreviated sectional side view of an electronic smoking article having a MAC insert constructed in accordance with another embodiment; wherein the MAC insert is in the form of a disc.

Referring now to FIG. 11, in another embodiment, the electronic smoking article 60 includes a gasket 10 having a central channel 63 as previously described with the other embodiments, together with a MAC insert 104*c*, which functions in a manner similar to that described with respect to the MAC insert 104 of the first embodiment with reference to FIGS. 1A and 1B. However, the MAC insert 104*c* of embodiment in FIG. 11 is in the form of a single disc having openings 112*c* radially spaced outwardly of a central face 102*c*. In this embodiment, the openings 112*c* and the face 102*c* are coplanar, whereas in the first embodiment shown in FIGS. 1A, 1B, 2 and 3, the face 102 is spaced upstream from the openings 112. Each opening 112*c* may have a diameter ranging from about 0.015 inch to about 0.090 inch (e.g., about 0.020 inch to about 0.040 inch or about 0.028 inch to about 0.038 inch).

Figure 13:
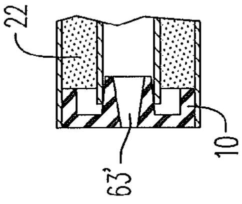
FIG. 13 is sectional side view of a detail of a gasket having a convergent outlet for inclusion in any of the foregoing embodiments.
Figure 12:
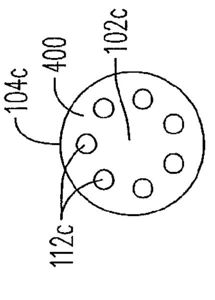
FIG. 12 is a planar view of the MAC insert as shown in FIG. 11.

Referring now to FIG. 13, in that higher velocities may enhance the benefits of impaction, expedients may be implemented to increase the speed of the aerosol as it approaches the face 102 of the MAC insert 104. For example, the gasket 10 can include a constricted central channel 63' to produce greater velocities in the aerosol as it is drawn through the central channel 63', and acts as an aerosol stream forming element.

Figure 14:
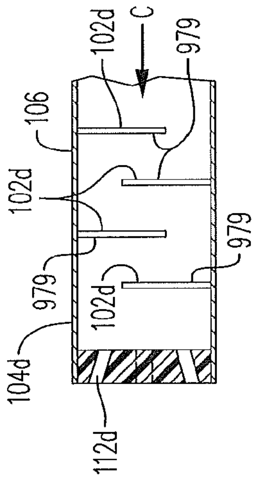
FIG. 14 is a cross sectional view of a MAC insert including a plurality of partitions therein.

Referring now to FIG. 14, in another embodiment, the MAC insert 104*d* comprises a cylindrical body 106 and a series of partitions 979 extending partially across the an interior of the cylindrical body 106 in alternating relationship. The partitions 979 are longitudinally spaced from one another and present multiple faces 102*d*, which aerosol may strike as aerosol passes through the MAC insert 104*d*. In this embodiment, the outlet orifices 112*d* are provided downstream of the partitions 979.

Optionally, the orifices 112, 112*a*, 112*b*, 112*c*, 112*d*, 112*e* in the embodiments of FIGS. 2, 3, 5A, 5B, 12, 14 and 15 may be sized to provide an RTD controlling aspect.

Figure 15:
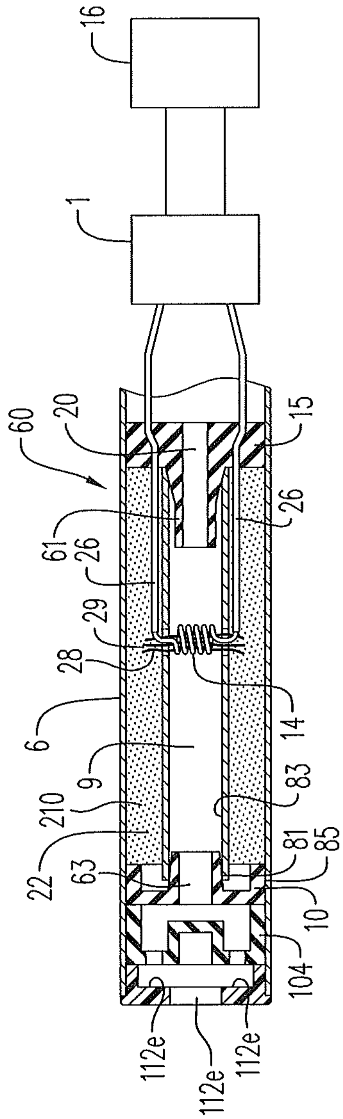
FIG. 15 is an abbreviated cross sectional side view of an electronic smoking article including another embodiment of a MAC insert.

Optionally, as shown in FIG. 15, it is contemplated that the relative, radial positions of the face 102*e* and the exit orifices 112*e* can be reversed such that an aerosol may be directed instead to an outer peripheral region of the MAC insert 104*e* and drawn through a central orifice 112*e*.

Optionally, the face 102, 102*a*, 102*b*, 102*c*, 102*d*, 102*e* of the MAC insert 104, 104*a*, 104*b*, 104*c*, 104*d*, 104*e* may be porous such that it has the capacity to collect particles through adsorption and/or absorption and in lieu of or in addition, may be concave in the upstream direction or in the downstream direction to adjust its characteristics as a mechanical aerosol converter.

Although the above teachings are with reference to a particular layout of an electronic smoking article 60, the teachings are equally applicable to any electronic smoking article whatever the configuration.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and nonobvious electronic smoking article has been described in this specification with sufficient particularity as to be understood by one of ordinary skill in the art. Moreover, it will be apparent to those skilled in the art that numerous modifications, variations, substitutions, and equivalents exist for features of the electronic smoking article which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. An electronic smoking article comprising:

an outer tube extending in a longitudinal direction;

an aerosol generator within the outer tube which produces a condensation aerosol within the outer tube; and a liquid supply within the outer tube delivering liquid material to the aerosol generator;

an aerosol stream forming element within the outer tube operable to produce an aerosol stream wherein the aerosol stream forming element comprises a gasket arranged such that the aerosol is drawn through a central orifice of the gasket; and a mouth end insert comprising a mechanical aerosol converter (MAC) insert disposed downstream of said gasket, said MAC insert arranged to impart impaction upon said aerosol stream as said aerosol is being drawn from said electronic smoking article, the MAC insert including three elongated exit orifices extending circumferentially about a perimeter of an exposed end surface of the MAC insert, said MAC insert comprising a face disposed upstream of said exposed end surface, said face being spaced from said central orifice, said face and said central orifice being arranged such that at least some of said aerosol stream drawn through said central orifice strikes said face, whereby a characteristic of said aerosol is altered.

2. The electronic smoking article of claim 1, wherein the three elongated exit orifices extending circumferentially about the perimeter of the exposed end surface are disposed radially outward of said face.

3. The electronic smoking article of claim 2, wherein said face is disposed within a cylindrical body, said face is spaced from an upstream edge portion of said cylindrical body, said edge portion abutting said gasket, whereby spacing between said face and said central orifice is consistently established.

4. The electronic smoking article of claim 1, wherein the characteristic of said aerosol is at least one of aerosol temperature and particle size distribution.

5. The electronic smoking article of claim 1, further comprising: an inner tube within the outer tube, wherein the aerosol generator comprises a heater located in the inner tube;

and a wick in communication with the liquid supply and surrounded by the heater such that the wick delivers liquid material to the heater and the heater heats the liquid material to a temperature sufficient to vaporize the liquid material and form an aerosol in the inner tube, wherein the liquid supply is contained in an outer annulus between the outer tube and the inner tube.

6. The electronic smoking article of claim 1, wherein the face is porous and particles of a predetermined size are retained on the face.

7. The electronic smoking article of claim 1, wherein the face is concave.

8. The electronic smoking article of claim 5, wherein the electronic smoking article comprises a first section attachable to a second section and wherein the wick, the heater and the liquid supply are contained in the first section and a power supply is contained in the second section.

9. The electronic smoking article of claim 5, wherein the outer tube is a single tube and the wick, the heater, the liquid supply and a power supply are contained in the outer tube.

10. The electronic smoking article of claim 1, wherein the liquid supply has a nicotine content of greater than 2% by weight based on the weight of the liquid supply.

11. The electronic smoking article of claim 1, wherein each of the three elongated exit orifices has a length ranging from about 2 mm to about 5 mm and a width ranging from about 0.5 mm to about 1 mm.

12. The electronic smoking article of claim 1, wherein the MAC insert is formed of plastic or metal foil.

13. The electronic smoking article of claim 1, wherein the MAC insert is in the form of a disk and the plurality of orifices are coplanar with the face of the MAC insert.

14. An electronic smoking article comprising: an outer tube extending in a longitudinal direction;

an aerosol generator within the outer tube which produces a condensation aerosol within the outer tube;

a liquid supply within the outer tube delivering liquid material to the aerosol generator;

an aerosol stream forming element within the outer tube operable to produce an aerosol stream through a central orifice; and a mechanical aerosol converter (MAC) insert comprising a monolithic cylindrical body portion having an outer diameter that is sized to provide a sliding fit with interior surfaces of the outer tube and a plurality of orifices disposed radially outward of a face, said face being aligned with and spaced from the central orifice of the aerosol stream forming element, wherein the face and inlets of the plurality of orifices are not coplanar, wherein the face of the MAC insert is arranged to impart impaction upon said aerosol stream and a characteristic of said aerosol is altered, as said aerosol is being drawn from said electronic smoking article.

15. The electronic smoking article of claim 14, wherein the aerosol generator is operable to heat a liquid material to a temperature sufficient to vaporize the liquid material to form an aerosol and the face of the MAC insert is arranged such that the characteristic of the aerosol which is altered upon impaction thereof with the face of the MAC insert is the temperature of the aerosol, wherein the temperature of the aerosol is reduced.

16. The electronic smoking article of claim 15, wherein the face of the MAC insert is arranged such that the temperature of the aerosol is reduced by 30° C. or more.

17. The electronic smoking article of claim 14, wherein the aerosol stream forming element comprises a gasket.

18. An electronic smoking article comprising: an outer tube extending in a longitudinal direction;

an aerosol generator within the outer tube which produces a condensation aerosol within the outer tube;

a liquid supply within the outer tube delivering liquid material to the aerosol generator;

an aerosol stream forming element within the outer tube operable to produce an aerosol stream, wherein the aerosol stream forming element comprises a constricted central channel operable to increase the velocity of the aerosol as it is drawn therethrough; and a mechanical aerosol converter (MAC) insert comprising a monolithic cylindrical body portion having an outer diameter that is sized to provide a sliding fit with interior surfaces of the outer tube and a plurality of orifices disposed radially outward of a face, said face being aligned with and spaced from the constricted channel of the aerosol stream forming element, wherein the face and inlets of the plurality of orifices are not coplanar, wherein the face of the MAC insert is arranged to impart impaction upon said aerosol stream, and a characteristic of said aerosol is altered, as said aerosol is being drawn from said electronic smoking article.

19. The electronic smoking article of claim 18, wherein the aerosol stream forming element comprises a gasket.

* * * * *